United States Patent
Dannecker et al.

(10) Patent No.: US 7,341,715 B2
(45) Date of Patent: *Mar. 11, 2008

(54) METHOD AND AGENTS ON THE BASIS OF 2-MERCAPTOPROPIONIC ACID AMIDES FOR DURABLE HAIR FORMING AND A METHOD FOR PRODUCING SAME

(75) Inventors: Beate Dannecker, Boeblingen (DE); Ursus Schweizer, Beerfelden (DE); Guenther Lang, Reinheim (DE); Regina Ortmann, Marburg (DE); Wolfgang Hanefeld, Lahn (DE)

(73) Assignee: Wella AG, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/979,965

(22) PCT Filed: May 21, 2001

(86) PCT No.: PCT/EP01/03388

§ 371 (c)(1),
(2), (4) Date: Nov. 27, 2001

(87) PCT Pub. No.: WO01/74318

PCT Pub. Date: Oct. 11, 2001

(65) Prior Publication Data

US 2003/0064043 A1    Apr. 3, 2003

(30) Foreign Application Priority Data

Apr. 1, 2000    (DE) ................ 100 16 406

(51) Int. Cl.
| | |
|---|---|
| A61Q 5/04 | (2006.01) |
| C07D 295/22 | (2006.01) |
| C07D 307/02 | (2006.01) |
| C07D 211/20 | (2006.01) |
| C07D 211/30 | (2006.01) |

(52) U.S. Cl. .................. 424/70.5; 424/70.1; 544/158; 544/159; 546/248; 549/280; 564/154

(58) Field of Classification Search ............... 424/70.1, 424/70.2
See application file for complete search history.

(56) References Cited

U.S. PATENT DOCUMENTS

| | | | |
|---|---|---|---|
| 3,576,592 A | 4/1971 | Zvlak et al. | |
| 3,619,106 A | 11/1971 | Kalopissis et al. | |
| 3,624,046 A | 11/1971 | Charle et al. | |
| 4,217,914 A | 8/1980 | Jacquet et al. | |
| 4,348,202 A | 9/1982 | Grollier et al. | |
| 4,422,853 A | 12/1983 | Jacquet et al. | |
| 4,579,732 A | 4/1986 | Grollier et al. | |
| 4,777,040 A | 10/1988 | Grollier et al. | |
| 4,948,579 A | 8/1990 | Jacquet et al. | |
| 4,970,066 A | 11/1990 | Grollier et al. | |
| 5,068,102 A * | 11/1991 | Tennigkeit et al. | |
| 5,196,189 A | 3/1993 | Jacquet et al. | |
| 6,264,932 B1 * | 7/2001 | Dannecker et al. | 424/70.2 |
| 6,399,051 B2 * | 6/2002 | Dannecker et al. | 424/70.5 |
| 2001/0056208 A1 | 12/2001 | Dannecker et al. | |

FOREIGN PATENT DOCUMENTS

| | | |
|---|---|---|
| EP | 0 455 457 A2 | 11/1991 |
| EP | 0 969 791 | 1/2000 |
| EP | 0 969 792 | 1/2000 |
| WO | 91/10421 | 7/1991 |
| WO | WO 9110421 A * | 7/1991 |
| WO | 99/06013 | 2/1999 |
| WO | 99/07330 | 2/1999 |

OTHER PUBLICATIONS

Voss, J. G.: "Skin Sensitization by Mercaptans . . . ", The Journal of Investigative Dermatology 31, 1958, pp. 273-279.
Protocol: Murine Local Lymph Node Assay, ICCVAM IWG LLNA Protocol, Jan. 2001, pp. 1-12.

* cited by examiner

*Primary Examiner*—Jyothsna Venkat
(74) *Attorney, Agent, or Firm*—Michael J. Striker

(57) ABSTRACT

The preparation for permanently deforming hair has a pH of 6.5 to 9.5 and contains, as keratin-reducing agent, a 2-mercaptopropion-amide of the formula (I):

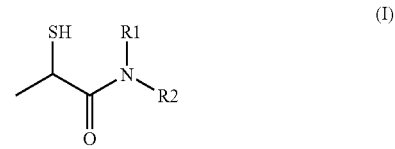

in which $R_1$ and $R_2$, independently of one another, represent H, a linear or branched alkylaminoalkyl group with 2 to 8 carbon atoms, or a morpholinoalkyl group with 2 to 3 carbon atoms in the alkyl portion of the morpholinoalkyl group, with the proviso that $R_1$ and $R_2$ are not simultaneously H, or that $R_1$ and $R_2$, together with the nitrogen atom, form a five-or six-membered heterocyclic ring, which optionally contain an additional N or O and are optionally substituted with one or two OH and/or methyl groups.

8 Claims, No Drawings

METHOD AND AGENTS ON THE BASIS OF 2-MERCAPTOPROPIONIC ACID AMIDES FOR DURABLE HAIR FORMING AND A METHOD FOR PRODUCING SAME

The present invention relates to a preparation for permanently deforming hair, which contains certain new 2-mercaptopropionamides as active, keratin-reducing agent, as well as to a method for permanently deforming hair using such agents.

It is well known that the classical technique for permanently deforming hair is based on two treatment steps. In the first step, the cystine disulfide bonds of the keratin of the hair are opened by the action of an agent, which contains a reducing agent (deformation preparation). The hair is then brought into the desired shape. In a second step, cystine disulfide bonds are formed once again, using a fixing agent, that is, a material containing an oxidizing agent.

The pioneering work of the German patents 948 186 and 972 424 shows that thioglycolic acid, for example, as the ammonium or monoethanolamine salt, is used as the classical permanent waving reducing agent. Inorganic sulfites, 2-mercaptopropinic acid (thiolactic acid), 3-mercaptopropionic acid, certain mercaptocarboxylate esters, cysteine and derivatives of these compounds are further conventional reducing agents.

However, all of these materials have a series of disadvantages. Although they have adequate activity, alkaline preparations, based on mercaptocarboxylic acids, damage the hair, for example, by increased breakages. These materials frequently also affect the scalp in an undesirable manner.

Finally, the unpleasant odor of the reducing agents employed makes intensive perfuming of the products necessary. Some of the problems mentioned can be eliminated by using 2-mercaptopropionic acid (thiolactic acid). However, in comparison to the generally used thioglycolic acid, the thiolactic acid is distinguished by a lesser ability to reshape.

The mercaptocarboxylate esters, which enable hair to be deformed even at low pH values, are not satisfactory with respect to their skin compatibility and the risk of sensitizing. Instead of mercaptocarboxylate esters, mercaptocarboxylamides, such as thioglycolamide or alkyl-substituted or hydroxyalkyl-substituted amides are also used. Such compounds are known from the patent literature, such as WO-A-91/10421 and EP-A-0 455 457. Like the carboxylate esters, these materials have a high re-shaping potential, even at low pH values. However, with respect to sensitizing, they are even more critical than the esters.

Surprisingly, it has now been found that the above disadvantages can be avoided by using certain 2-mercaptopropionamides and that the re-shaping potential of the latter exceeds that of thiolactic acid.

The object of the present invention therefore is a preparation for permanently deforming hair, wherein, as keratin-reducing agent, the preparation contains a 2-mercaptopropionamide of the general formula

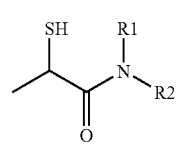

(I)

in which $R_1$ and $R_2$ independently of one another represent H, a linear or branched alkyl group with 1 to 4 carbon atoms, a linear or branched mono- or dihydroxyalkyl group with 2 to 4 carbon atoms, a linear or branched alkoxyalkyl group or alkylaminoalkyl group with 2 to 8 carbon atoms, morpholinoalkyl with 2 to 3 carbon atoms in the alkyl group, with the proviso that $R_1$ and $R_2$ are not simultaneously H, or that $R_1$ and $R_2$, together with the nitrogen atom, form a five- or six-membered heterocyclic ring, which may contain a further N or O and be substituted with one or two OH and/or methyl groups.

Preferred compounds of formula (I) are those, in which $R_1$ and $R_2$ independently of one another represent H, —$CH_3$, —$CH_2CH_2CH_3$, —$CH(CH_3)_2$, $CH_2CH_2OH$, —$CH_2CH(OH)CH_3$, —$CH(CH_2CH_3)(CH_2OH)$, —$CH_2CH_2CH_2N(CH_3)_2$, —$CH_2CH_2OCH_3$, —$CH_2CH_2CH_2OCH_3$, —$CH_2CH_2N(CH_2CH_3)_2$, —$CH_2CH_2N(CH_3)_2$ or morpholinoalkyl with 2 to 3 carbon atoms in the alkyl group, with the proviso that $R_1$ and $R_2$ do not simultaneously represent H.

Particularly preferred compounds are those having the formulas

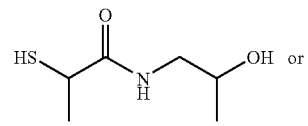

(II)

or

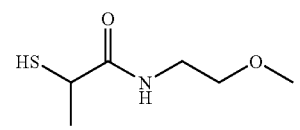

(III)

The inventive 2-mercaptopropionamides are synthesized by reacting the appropriate amine with methyl 2-mercaptopropionate under an inert gas atmosphere, followed by extraction with a suitable solvent and subsequent molecular distillation.

The 2-mercaptopropionamides of formula (I) are used in the ready-for-use preparations for permanently deforming hair in an amount of 3 to 28% by weight and preferably of 5 to 21% by weight.

In a further embodiment, the inventive 2-mercaptopropionamides can also be used in a mixture with other known thiols, such as thioglycolic acid, thiolactic acid, cysteine, cysteamine and alkyl- or acylcysteamines or sulfites.

The ready-for-use hair deformation material preferably has a pH of 6.5 to 9.5 and especially of 6.5 to 8.5. As alkalizing agent or as a material for adjusting the pH, especially ammonia or sodium hydroxide solution, but also all other water-soluble, physiologically compatible salts of organic and inorganic bases, such ammonium hydrogen carbonate, come into consideration.

The deformation material can be packaged as a one-component, as well as a two-component material. If packaged as a two-component material, the two components are mixed together immediately before use. The material may be in the form of an aqueous solution or an emulsion, as well as in thickened form on an aqueous basis, especially as a cream, gel, foam or paste.

Of course, the deformation material may contain all additives, which are customary and known for such materials, for example, thickeners such as bentonite, fatty acids, starch, polyacrylic acid and their derivatives, cellulose derivatives, alginates, Vaseline, paraffin oils, wetting agents or emulsifiers from the classes of anionic, cationic, amphoteric or nonionic surface active substances, such as fatty alcohol sulfates, fatty alcohol ether sulfates, alkyl sulfonates, alkylbenzenesulfates, quaternary ammonium salts, alkylbetaines, ethoxylated alkylphenols, fatty acid alkanolamides or ethoxylated fatty esters, furthermore opacifiers, such as polyethylene glycol esters, alcohols, such as ethanol, propanol, isopropanol and glycerin, sugars such as D-glucose, solubilizers, stabilizers, buffers, perfume oils, dyes as well as hair conditioning and hair care components, such as cationic polymers, lanolin derivatives, cholesterol, pantothenic acid and betaine.

The components mentioned are used in amounts suitable for such purposes. For example, the wetting agents and emulsifiers are used in concentrations totaling 0.2 to 30% by weight, the alcohols in an amount totaling 0.1 to 20% by weight, the alcohols in an amount totaling 0.1 to 20% by weight, the opacifiers, perfume oils and dyes in an amount in each case of 0.01 to 1% by weight, the buffers in an amount totaling 0.1 to 10% by weight, sugars, solubilizers, stabilizers as well as hair conditioning and hair care components in an amount in each case of 0.1 to 5% by weight, while the thickeners and solubilizing agents may be contained in this material in an amount totaling 0.5 to 20% by weight.

Furthermore, to increase the effect, swelling and penetrating materials, such as dipropylene glycol monomethyl ether, 2-pyrrolidone or 2-imidazolidinone in an amount of 1 to 30% by weight, as well as, to avoid excessive curling of the hair, dithio compounds, such as dithiodiglycolic acid, dithiolactic acid, the dithiols of compounds of formula (I) or the respective salts of the dithiols, can be added to these materials.

By varying the pH, a material can be made available, which is suitable universally for any hair structure, optionally with additional action of heat. The material brings about an elastic, permanent and uniform reshaping of hair from the root to the tip, without causing allergic or sensitizing reactions.

The present invention furthermore relates to a method for permanently waving hair, for which the hair, before and/or after it is brought into the desired shape, is treated with a deforming material, rinsed with water, then treated oxidatively, optionally laid into a water wave and then dried, wherein an inventive material, described above, is used as deforming material.

In a preferred embodiment of the inventive method, the hair is initially washed with a shampoo and then rinsed with water. Subsequently, the towel-dried hair is divided into individual strands and wound onto curlers with a diameter of 5 to 30 millimeters and preferably of 5 to 15 millimeters. The hair is then treated with an amount, preferably of 60 to 120 gram, of the described inventive deformation material, sufficient for deforming it.

After a period of action, which is sufficient for the permanent deformation of the hair and which, depending on the nature of the hair, the pH and the deformation effectiveness of the waving material as well as on the application, is 5 to 30 minutes (10 to 30 minutes without the action of heat, 5 to 20 minutes with the action of heat), the hair is rinsed with water and then given an oxidative after-treatment ("fixed"). The material for the after-treatment is used in an amount preferably of 80 to 100 gram, depending on the fullness of the hair.

For the oxidative after-treatment in the curled or uncurled state, any after-treatment agent, suitable for such a treatment, can be used. Examples of oxidizing agents, which can be used in such after-treatment agents, are potassium and sodium bromate, sodium perborate and urea peroxide and hydrogen peroxide. The concentration of the oxidizing agent varies, depending on the application time (usually 5 to 15 minutes) and the application temperature. Normally, the oxidizing agent is present in the ready-for-use aqueous after-treatment material in a concentration of 0.5 to 10% by weight. The agent for the oxidative after-treatment can, of course, also contain other materials, such as wetting agents, care materials such as cationic polymers, weak acids, buffers or peroxide stabilizers and be in the form of an aqueous solution, an emulsion as well as in thickened, aqueous form, particularly in the form of a cream, gel or paste. These usual additives may be contained especially in an amount of 0.1 to 10% by weight of the after-treatment agent.

Subsequently, the curlers are removed. If necessary, the hair, removed from the curlers, can be treated once again oxidatively. The hair is then rinsed with water, optionally laid into a water wave and finally dried.

The following examples are intended to explain the object of the invention in greater detail.

SYNTHESIS METHODS

Synthesis of 2-Mercaptopropionamide by Method A

The respective amine (2 to 3 moles) is added to a 500 mL 3-neck flask. While cooling in a waterbath, 1 mole of methyl 2-mercaptopropionate is slowly added dropwise, so that the temperature does not exceed 30° C. The mixture is flushed with argon and then stirred (optionally with slight heating), until the ester has been reacted quantitatively (checked by IR spectroscopy). The mixture, cooled in ice, is acidified with 32% hydrochloric acid (pH 2 to 4) and extracted exhaustively with ethyl acetate or t-butyl methyl ether. The solvent is distilled off under vacuum in a rotary evaporator, the residue adjusted to a pH of 7.0 by the addition of sodium hydroxide solution and extracted once again exhaustively with ethyl acetate or t-butyl methyl ether. The combined fractions are dried over sodium sulfate and concentrated. The residue is distilled with the help of molecular distillation equipment (parallel flow distillation) at about 0.02 mbar or recrystallized from a suitable solvent to a largely pure product or purified by column chromatography.

Synthesis of 2-Mercaptopropionamide by Method B

The respective amine (2 moles) is added to a 500 mL 3-neck flask. While cooling in a waterbath, 1 mole of methyl 2-mercaptopropionate is slowly added dropwise, so that the temperature does not exceed 30° C. The mixture is flushed with argon and then stirred (optionally with slight heating), until the ester has been reacted quantitatively (checked by IR spectroscopy). Subsequently, the excess amine is distilled off at about 1 mbar. The residue is distilled at about 0.08 mbar over a Vigreux column or distilled by means of molecular distillation equipment (parallel flow distillation) at about 0.02 mbar or recrystallized from a suitable solvent to a largely pure product.

Synthesis of 2-Mercaptopropionamide by Method C

The respective amine (2 moles) is added to a 1 L 3-neck flask. While cooling in a waterbath, 1 mole of methyl 2-mercaptopropionate is slowly added dropwise, so that the temperature does not exceed 30° C. The mixture is then stirred, until the ester has been reacted quantitatively (checked by IR spectroscopy). Subsequently, while cooling in a waterbath, 1 mole of potassium ethyl xanthogenate is spooned in. The mixture is stirred for a further two hours with cooling in a waterbath and a further 2 hours at room temperature. Ammonia solution (500 mL, 25%) is then added and stirring is continued for a further 24 hours.

The ammoniacal solution is extracted with ethyl acetate. The aqueous phase is cooled in ice and acidified with 32% hydrochloric acid (pH 2 to 4) and extracted exhaustively with ethyl acetate. The solvent is evaporated under vacuum in a rotary evaporator and the residue, after its pH is adjusted to 7.0 by the addition of sodium hydroxide solution, is extracted exhaustively once again with ethyl acetate. The combined fractions are dried over sodium sulfate and concentrated. The residue is distilled with the help of a molecular distillation apparatus (parallel flow distillation) at about 0.02 mbar or recrystallized from a suitable solvent to a largely pure product.

Synthesis of 2-Mercaptopropionamide by Method D

The respective amine (1 mole) in a 1 L 3-neck flask is treated with 500 mL of 2N sodium hydroxide solution and cooled to 0° C. in an ice and salt bath. 2-Chloropropionyl chloride (1 mole) is added dropwise in such a way, that the temperature does not exceed 5° C. The mixture is stirred vigorously for three hours at room temperature. Subsequently, while cooling in a waterbath, 1 mole of potassium ethyl xanthognate is spooned in. The mixture is stirred for a further two hours with cooling in a waterbath and an additional two hours at room temperature. The mixture is acidified with 32% hydrochloric acid, until a yellow oil separates out. This oil is separated, treated with 500 mL of a 25% ammonia solution and stirred for a further 24 hours.

The ammoniacal solution is extracted with ethyl acetate. The aqueous phase is cooled with ice, acidified with 32% hydrochloric acid (ph 2 to 4) and extracted exhaustively with ethyl acetate. The solvent is evaporated under vacuum in a rotary evaporator, the pH of the residue is adjusted to 7.0 by the addition of sodium hydroxide solution and the residue is extracted exhaustively once again with ethyl acetate. The combined fractions are dried over sodium sulfate and evaporated. The residue is distilled at 0.02 mbar using molecular distillation equipment (parallel flow distillation) or recrystallized from a suitable solvent to a largely pure product.

Comparison of the Stabilities of the Waves

The waving effectiveness of the 1-mercaptopropionamides was determined using glycerin monothioglycolate as comparison substance with the help of waving solutions at a pH of 7, 8 and 9. For this purpose, pre-bleached and therefore damaged counting hair strands (consisting of about 100 hairs) from Middle European hair was wound wet onto standardized spiral curlers (internal diameter of 3 millimeters) and, after being conditioned in an air-conditioned room (temperature: 20° C., relative humidity: 65%), treated with a solution of the reducing agent, containing 87 mmoles/100 g and adjusted to the respective pH. The amount of waving liquid applied was calculated from the ratio of 1:1.2 (1 g of hair: 1.2 mL of waving liquid). A period of action of 20 minutes at a temperature of 50° C. was selected. Subsequently, the hair was fixed with a peroxide-containing material, removed from the curlers and hung up for 4 hours in water (waterbath temperature: 40° C.).

The wave stability (WSN) is calculated from the following formula:

$$\text{Wave stability in \%} = \frac{I_0 - I_t}{I_0 - I_1} \times 100$$

$I_o$=total length of the not shaped, stretched strands (16.5 cm)

$I_t$=length of the strands, removed from the curlers and suspended, after 240 minutes $I_1$=length of the shaped strands on curlers (for curlers with an internal diameter of 3 mm, $I_1$=35 mm)

As a standard, strands were treated with a glycerin monothioglycolate solution, the pH of which had been adjusted to a value of 9. The standardized wave stabilities, given below in Table 1, relate to this standard solution (pH=9), the wave stability (WSN) of which has been set at 100%.

EXAMPLE 1

Synthesis of 2-Mercaptopropionamide by Method A

1-Amino2-propanol (150 g, 2 moles) and 120 g (1 mole) of methyl 2-mercaptopropionate are reacted by Method A. The product is purified by distillation at 110° C. and 0.02 torr. The yield of 83.6 g is 51% of the theoretical yield.

Analysis a) $^1$H-NMR (CDCl$_3$):
 δ (ppm) = 7.02 (bs, 1H, N$\underline{H}$)
 3.96 (m, 1H, C$\underline{H}$—OH)
 3.45 (m, 2H, C$\underline{H}$2-NH)
 3.15 (m, 1H, C$\underline{H}$—SH)
 3.01 (bs, 1H, O$\underline{H}$)
 2.12 (bs, 1H, S$\underline{H}$)
 1.55 (d, 3H, SH—CH—C$\underline{H}_3$)
 1.21 (d, 3H, OH—CH—C$\underline{H}_3$)

b) $^{13}$C—NMR (CDCl$_3$):
 δ (ppm) = 174.13 ($\underline{C}$O)
 67.20 ($\underline{C}$H—OH)
 47.25 (NH—$\underline{C}$H$_2$)
 38.14 (HS—$\underline{C}$H)
 22.20 (HS—CH—$\underline{C}$H$_3$)
 20.91 (HO—CH—$\underline{C}$H$_3$)

c) MS (70 eV, EI, 150° C.):
 m/z (%) = (M+) 163 (42)
 119 (100), 106 (41), 102 (28), 86(97), 85 (23), 84 (83), 61 (47), 58 (33), 56 (27)

d) Thiol titration: 99.1% e) Elementary analysis: C$_6$H$_{12}$NO$_2$S  (MW: 163.24 g/moles)
 Calc.: C 44.15  H 3.03  N 8.58  S 19.64
 Found: C 43.44  H 8.06  N 8.40  S 19.57

-continued

| | Analysis | | |
|---|---|---|---|
| f) | IR (NaCl plates): | | |
| | | 3307 cm$^{-1}$ | (OH) |
| | | 2976 cm$^{-1}$ + 2931 cm$-1$ | (CH$_2$) |
| | | 2543 cm$^{-1}$ | (SH) |
| | | 1653 cm$^{-1}$ | (N-monosubstituted amide) |
| | | 1556 cm$^{-1}$ | (N-monosubstituted amide) |
| HPLC: | relative purity: | 97.8 area percent | |
| | retention time: | 3.0 min | |
| | column: | Adsorbosphere C 18 5U, 250 mm × 4.6 mm | |
| | Solvent: | acetonitrile buffer = 25:75 | |
| | | (buffer: 4 g potassium dihydrogen phosphate + | |
| | | 0.8 g octanesulfonic acid, sodium salt + | |
| | | 2 mL phosphoric acid per 1 L water for | |
| | | HPLC) | |
| | flow rate: | 1 mL/min | |
| | wavelength: | 202 nm | |
| g) | 197 nm (acetonitrile: buffer = 25:75 | | |
| h) | pKa value: 8.37 | | |
| i) | melting point: 40° C. | | |

The Tables below show that the waving effectiveness of the inventive 2-mercaptopropionamides at a pH of 7, 8 and 9 is higher than that of thiolactic acid.

| Amine Component Propionamide | Analysis calc./found | HPLC (Area percent) | Boiling Point | WSN pH = 7 | WSN pH = 8 | WSN pH = 9 | Synthesis Method | Yield |
|---|---|---|---|---|---|---|---|---|
| 1-Amino-2-propanol | C: 44.15%, H: 8.03% N: 8.58%, S: 19.64% | 97.8% | (melting point: 40° C.) | 78% | 94% | 94% | A | 51% |
| | C: 43.44%, H: 8.06% N: 8.40%, S: 19.57% | | | | | | | |
| N-(2-Hydroxypropyl)-2-mercapto-propionamide | C: 43.42%, H: 7.71% N: 8.44%, S: 19.65% | 93.0% | 110° C. (0.02 Torr) | | | | C | 34% |
| 2-Amino-2-methyl-1-propanol | C: 47.43%, H: 8.53% N: 7.90%, S: 18.09% | 97.1% | (melting point: 70° C.) | 79% | 91% | 94% | A | 28% |
| | C: 47.70%, H: 8.40% N: 8.01%, S: 17.92% | | | | | | | |
| N-(2-Hydroxy-1-butyl)-2-mercapto-propionamide | C: 47.49%, H: 8.36% N: 8.05%, S: 17.85% | 99.4% | (melting point: 63° C.) | | | | C | 26% |
| 2-Amino-1-butanol | C: 47.43%, H: 8.53% N: 7.90%, S: 18.09% | 96.9% | (melting point: 56° C.) | 73% | 88% | 85% | A | 20% |
| N-(1-Hydroxymethylpropyl)-2-mercaptopropionamide | C: 47.51%, H: 7.89% N: 7.75%, S: 17.94% | | | | | | | |
| 2-Amino-2-methyl-1,3-propanediol | C: 43.50%, H: 7.82% N: 7.25%, S: 16.59% | 93.0% | (melting point: 138° C.) | | | | A | 20% |
| [1,1-Bis(hydroxymethyl)-ethyl]-2-mercaptopropionamide | C: 43.47%, H: 7.60% N: 7.22%, S: 16.17% | | | | | | | |
| Ethanolamine | C: 40.25%, H: 7.43% N: 9.39%, S: 21.49% | 100% | (melting point: 56° C.) | 84% | 106% | 103% | A | 32% |
| N-(2-Hydroxyethyl)-2-mercapto-propionamide | C: 40.16%, H: 7.30% N: 9.43%, S: 21.06% | | | | | | | |
| Methylaminoethanol | C: 44.15%, H: 8.03% N: 8.58%, S: 19.64% | 97.3% | 95° C. (0.02 Torr) | 72% | 91% | 91% | A | 38% |
| N-Methyl,N-(2-hydroxyethyl)-2-mercaptopropionamide | C: 44.33%, H: 8.06% N: 8.60%, S: 19.84% | | | | | | | |
| Ethylaminoethanol | C: 47.43%, H: 8.53% N: 7.90%, S: 18.09% | 94.7% | 95° C. (0.02 Torr) | 94% | 83% | 114% | A | 68% |
| | C: 47.23%, H: 8.16% N: 8.01%, S: 17.84% | | | | | | | |
| N-Ethyl,N-(2-hydroxyethyl)-2-mercaptopropionamide | C: 47.36%, H: 8.28% N: 7.88%, S: 17.88% | 95.5% | 95° C. (0.02 Torr) | | | | C | 29% |
| Propylaminoethanol | C: 50.23%, H: 8.96% N: 7.32%, S: 16.76% | 96.5% | 80° C. (0.02 Torr) | 77% | 89% | 99% | A | 48% |
| N-Propyl,N-(2-hydroxyethyl)-2-mercaptopropionamide | C: 50.10%, H: 8.70% N: 7.33%, S: 16.81% | | | | | | | |
| Isopropylaminoethanol | C: 50.23%, H: 8.96% N: 7.32%, S: 16.76% | 98.0% | 100° C. (0.02 Torr) | 65% | 88% | 109% | A | 54% |
| N-Isopropyl,N-(2-hydroxyethyl)-2-mercaptopropionamide | C: 49.97%, H: 8.52% N: 7.24%, S: 16.80% | | | | | | | |

-continued

| Amine Component<br>Propionamide | Analysis<br>calc./found | HPLC<br>(Area percent) | Boiling Point | WSN pH = 7 | WSN pH = 8 | WSN pH = 9 | Synthesis Method | Yield |
| --- | --- | --- | --- | --- | --- | --- | --- | --- |
| 3-Hydroxypiperidine | C: 50.77%, H: 7.99%<br>N: 7.40%, S: 16.94% | 97.6%<br>(thiol titr.) | 110° C.<br>(0.02 Torr) | 79% | 94% | 89% | D | 21% |
| N,N-[3-Hydroxy-pentamethylene]-2-mercaptopropionamide | C: 49.62%, H: 7.99%<br>N: 7.38%, S: 17.47% | | | | | | | |
| 2-Methoxyethylamine | C: 44.15%, H: 8.03%<br>N: 8.58%, S: 19.64% | 98.3% | 85° C.<br>(0.08 mbar) | 87% | 99% | 106% | A | 67% |
| N-(2-Methoxyethy)-2-mercapto-propionamide | C: 44.05%, H: 7.95%<br>N: 8.47%, S: 19.52% | | | | | | | |
| 3-Methoxypropylamine | C: 47.43%, H: 8.53%<br>N: 7.90%, S: 18.09% | 98.4% | 97° C.<br>(0.08 mbar) | 79% | 92% | 91% | A | 69% |
| N-(3-Methoxypropyl)-2-mercapto-propionamide | C: 47.15%, H: 8.24%<br>N: 7.80%, S: 17.94% | | | | | | | |
| Tetrahydrofurfurylamine | C: 50.77%, H: 7.99%<br>N: 7.40%, S: 16.94% | 98.6%<br>(thiol titration) | 82° C.<br>(0.06 mbar) | 85% | 88% | 94% | A | 75% |
| N-Tetrahydrofurfuryl-2-mercapto-propionamide | C: 50.75%, H: 7.99%<br>N: 7.35%, S: 16.56% | | | | | | | |
| 2-Amino-1-methoxypropane | C: 47.43%, H: 8.53%<br>N: 7.90%, S: 18.09% | 98.2% | 60° C.<br>(0.06 mbar) | 91% | 95% | 99% | D | 15% |
| N-(1-Methoxy-2-propyl)-2-mercapto-propionamide | C: 47.52%, H: 8.35%<br>N: 8.22%, S: 18.26% | | | | | | | |
| Bis-(2-methoxyethyl)-amine | C: 48.84%, H: 8.65%<br>N: 6.33%, S: 14.49% | 97.5% | 85° C.<br>(0.06 mbar) | 78% | 93% | 91% | D | 32% |
| N,N-Bis-(2-methoxyethyl)-2-mercapto-propionamide | C: 48.71%, H: 8.64%<br>N: 6.58%, S: 14.65% | | | | | | | |
| Morpholine | C: 47.98%, H: 7.48%<br>N: 7.99%, S: 18.30% | 98.2% | 80° C.<br>(0.02 Torr) | 83% | 93% | 96% | A | 27% |
| N,N-3-Oxa-pentamethylene-2-mercaptopropionamide | C: 47.74%, H: 7.37%<br>N: 7.78%, S: 17.98% | | | | | | | |
| N-Methylpiperazine | C: 51.03%, H: 8.56%<br>N: 14.88%, S: 17.03% | 97.5% | 98° C.<br>(0.1 mbar) | 78% | 86% | 78% | B | 15% |
| N,N-(4-Methylaza-pentamethylene)-2-mercaptopropionamide | C: 50.84%, H: 8.34%<br>N: 14.80%, S: 16.43% | | | | | | | |
| 3-Dimethylaminopropylamine | C: 50.49%, H: 9.53%<br>N: 14.72%, S: 16.85% | 98.1% | 84° C.<br>(0.05 mbar) | 72% | 83% | 95% | B | 72% |
| N-(3-Dimethylaminopropyl)-2-mercaptopropionamide | C: 50.12%, H: 9.31%<br>N: 14.78%, S: 16.85% | | | | | | | |
| 3-Diethylaminopropylamine | C: 55.00%, H: 10.16%<br>N: 12.83%, S: 14.68% | 97.4% | 65° C.<br>(0.02 Torr) | 77% | 73% | 81% | B | 81% |
| N-(3-Diethylaminopropyl)-2-mercapto-propionamide | C: 54.53%, H: 9.68%<br>N: 12.55%, S: 14.40% | | | | | | | |
| 3-(Methylamino)-propylamine | C: 47.69%, H: 9.15%<br>N: 15.89%, S: 18.19% | 98.8%<br>(thiol titr.) | (melting point: 99° C.) | 55% | 73% | 78% | B | 45% |
| N-(3-Methylaminopropyl)-2-mercapto-propionamide | C: 47.75%, H: 9.10%<br>N: 15.20%, S: 18.06% | | | | | | | |
| 2-Dimethylaminoethylamine | C: 47.69%, H: 9.15%<br>N: 15.89%, S: 18.19% | 98.4% | 83° C.<br>(0.06 mbar) | 81% | 87% | 83% | B | 79% |
| N-(2-Dimethylaminoethyl)-2-mercapto-propionamide | C: 47.05%, H: 9.05%<br>N: 14.95%, S: 17.80% | | | | | | | |
| 2-Diethylaminoethylamine | C: 52.90%, H: 9.87%<br>N: 13.71%, S: 15.69% | 99.3% | 74° C.<br>(0.06 mbar) | 71% | 80% | 77% | B | 81% |
| N-(2-Diethylaminoethyl)-2-mercaptopropionamide | C: 52.84%, H: 9.72%<br>N: 13.38%, S: 15.36% | | | | | | | |
| 2-(Ethylamino)-ethylamine | C: 47.69%, H: 9.15%<br>N: 15.89%, S: 18.19% | 98.1% | (melting point: 82° C. | 57% | 82% | 60% | B | 53% |
| N-(2-Ethylaminoethyl)-2-mercaptopropionamide | C: 47.69%, H: 8.86%<br>N: 15.78%, S: 18.19% | | | | | | | |
| Ethylenediamine | C: 40.51%, H: 8.16%<br>N: 18.90%, S: 21.63% | 96.7%<br>(thiol titr.) | (melting point: 121° C.) | 61% | 81% | 87% | B | 39% |
| N-(2-Aminoethyl)-2-mercaptopropionamide | C: 40.52%, H: 8.06%<br>N: 17.92%, S: 21.41% | | | | | | | |
| 4-(2-Aminoethyl)-morpholine | C: 49.51%, H: 8.31%<br>N: 12.83%, S: 14.68% | 98.6%<br>(thiol titr.) | (melting point: 75° C.) | 85% | 93% | 92% | B | 46% |
| N-(2-Morpholinoethyl)-2-mercaptopropionamide | C: 49.41%, H: 7.94%<br>N: 12.65%, S: 14.78% | | | | | | | |
| 1,3-Diaminopropane | C: 44.41%, H: 8.70%<br>N: 17.27%, S: 19.76% | 98.9%<br>(thiol titr.) | (melting point: 143° C.) | 67% | 82% | 88% | B | 79% |
| N-(3-Aminopropyl)-2-mercaptopropionamide | C: 44.25%, H: 8.67%<br>N: 16.95%, S: 20.01% | | | | | | | |
| Thiolactic acid as comparison | | | | 57% | 50% | 70% | | |

EXAMPLE 2

| | |
|---|---|
| 13.2 g | N-(2-hydroxypropyl)-2-mercaptopropionamide |
| 0.4 g | ammonia (25% watery solution) for adjusting the pH |
| 2.0 g | ammonium hydrogen carbonate |
| 2.0 g | isopropanol |
| 1.0 g | isooctylphenol, ethoxylated with 10 moles of ethylene oxide |
| 1.0 g | poly(dimethyldiallyl ammonium chloride) |
| 0.3 g | perfume oil |
| 0.1 g | vinylpyrrolidone / styrene copolymer (Antara ® 430 of GAF Corp., New York/USA) |
| 80.0 g | water |
| 100.0 g | |

The pH of this agent is between 7.0 and 7.5.

Hair, which has been damaged by dyeing treatments, is washed with a shampoo, toweled dry and wound onto curlers with a diameter of 8 millimeters. Subsequently, the hair-deformation agent, described above, is distributed uniformly on the curled hair. The hair is then covered with a plastic cap and heated for 10 minutes under a drying hood at a temperature of 45° C. Subsequently, the covering is removed, the hair is rinsed with water and treated oxidatively with 100 g of a 3% aqueous hydrogen peroxide solution. After the curlers are removed, the hair once again is rinsed with water, laid into a water wave and then dried. As a result of this treatment, a uniform, elastic and permanently waved hair is obtained.

EXAMPLE 3

Permanent Waving Agent for Normal Hair

| | |
|---|---|
| 18.0 g | N-(2-hydroxypropyl)-2-mercaptopropionamide |
| 8.9 g | ammonia (25% watery solution) |
| 5.0 g | ammonium hydrogen carbonate |
| 4.0 g | urea |
| 2.4 g | monoethanolamine |
| 1.5 g | isooctylphenol, ethoxylated with 10 moles of ethylene oxide |
| 0.5 g | poly(dimethyldiallyl ammonium chloride) |
| 0.5 g | perfume oil |
| 0.1 g | vinylpyrrolidone / styrene copolymer (Antara ® 430 of GAF Corp., New York/USA) |
| 59.1 g | water |
| 100.0 g | |

The pH of this agent is 8.4.

Normal, undamaged hair is washed, dried with a towel and wound onto rollers with a diameter of 6 mm. Subsequently, the hair is moistened uniformly with the hair-waving agent described above. After a period of action of 15 minutes, the hair is rinsed thoroughly with water and then treated oxidatively with 80 gram of a 3% aqueous solution of hydrogen peroxide. After the curlers are removed, the hair is rinsed once again with water, laid into a water wave and subsequently dried. The hair, so treated, has a uniform and lively curl.

EXAMPLE 4

Permanent Waving Agent for Normal Hair

| | |
|---|---|
| 10.0 g | N-(1-hydroxymethylpropyl)-2-mercaptopropionamide |
| 8.9 g | ammonia (25% watery solution) for adjusting the pH |
| 5.0 g | ammonium hydrogen carbonate |
| 2.0 g | D-glucose |
| 2.4 g | ammonia |
| 1.5 g | isooctylphenol, ethoxylated with 10 moles of ethylene oxide |
| 0.5 g | poly(dimethyldiallyl ammonium chloride) |
| 0.5 g | perfume oil |
| 0.1 g | vinylpyrrolidone / styrene copolymer (Antara ® 430 of GAF Corp., New York/USA) |
| 61.1 g | water |
| 100.0 g | |

The pH of this agent is 8.0 to 8.5.

Normal, undamaged hair is washed, dried with a towel and wound onto rollers with a diameter of 6 mm. Subsequently, the hair is moistened uniformly with the hair-waving agent described above. After a period of action of 15 to 25 minutes, the hair is rinsed thoroughly with water and then treated oxidatively with 80 gram of a 3% aqueous solution of hydrogen peroxide. After the curlers are removed, the hair is rinsed once again with water, laid into a water wave and subsequently dried. The hair, so treated, has a uniform and lively curl.

The invention claimed is:

1. A preparation for permanently deforming hair having a pH of 6.5 to 9.5 and containing, as keratin-reducing agent, a 2-mercapto-propionamide of the formula (I):

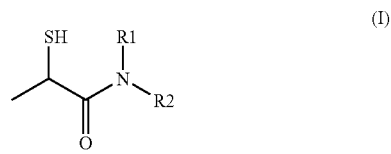

in which $R_1$ and R2, independently of one another, represent H, a linear or branched alkylaminoalkyl group with 2 to 8 carbon atoms, or a morpholinoalkyl group with 2 to 3 carbon atoms in the alkyl portion of the morpholinoalkyl group, or in which $R_1$ and R2, together with the nitrogen atom, form a five- or six-membered heterocyclic ring, which optionally contain an additional N or 0 and are optionally substituted with one or two OH and/or methyl groups with the proviso that R1 and R2 are not simultaneously H.

2. The preparation as defined in claim 1, containing from 3 to 28% by weight of the 2-mercaptopropionamide of formula (I).

3. The preparation as defined in claim 1, obtained by mixing two or three components.

4. A method for permanently deforming hair, wherein the hair, before and/or after the hair is held in a desired shape, is treated with a deforming preparation, rinsed with water, then treated oxidatively, rinsed once again with water, optionally laid into a water wave and then dried, wherein said deforming preparation has a pH of 6.5 to 9.5 and contains, as keratin-reducing agent, a 2-mercaptopropiona-mide of the formula (I):

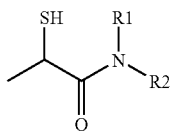
(I)

in which $R_1$ and R2, independently of one another, represent H, a linear or branched alkylaminoalkyl group with 2 to 8 carbon atoms, or a morpholinoalkyl group with 2 to 3 carbon atoms in the alkyl portion of the morpholinoalkyl group, or in which $R_1$ and R2, together with the nitrogen atom, form a five- or six-membered heterocyclic ring, which optionally contain an additional N or 0 and are optionally substituted with one or two OH and/or methyl groups with the proviso that R1 and R2 are not simultaneously H.

5. The method as defined in claim 4, wherein the deforming preparation is allowed to act on the hair for 10 to 30 minutes without heating the hair.

6. The method as defined in claim 4, wherein the deforming preparation is allowed to act on the hair for 5 to 20 minutes with heating the hair.

7. The method as defined in claim 4, wherein the hair is treated with from 60 to 120 gram of the deforming preparation.

8. A 2-mercaptopropionamide of the formula (I):

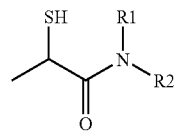
(I)

in which $R_1$ and R2, independently of one another, represent H, a linear or branched alkylaminoalkyl group with 2 to 8 carbon atoms, or a morpholinoalkyl group with 2 to 3 carbon atoms in the alkyl portion of the morpholinoalkyl group, or in which $R_1$ and R2, together with the nitrogen atom, form a five- or six-membered heterocyclic ring, which optionally contain an additional N or 0 and are optionally substituted with one or two OH and/or methyl groups with the proviso that R1 and R2 are not simultaneously H.

* * * * *